(12) United States Patent
Tinker

(10) Patent No.: US 7,090,184 B2
(45) Date of Patent: Aug. 15, 2006

(54) MEDICAL VENTILATOR BAG AND MASK MOUNT

(76) Inventor: Douglas R. Tinker, 420 Avenue G, #13, Redondo Beach, CA (US) 90277

( * ) Notice: Subject to any disclaimer, the term of this patent is extended or adjusted under 35 U.S.C. 154(b) by 0 days.

(21) Appl. No.: 10/384,084

(22) Filed: Mar. 7, 2003

(65) Prior Publication Data

US 2004/0173214 A1    Sep. 9, 2004

(51) Int. Cl.
*A47F 5/00* (2006.01)
*A61M 16/00* (2006.01)
(52) U.S. Cl. ............... 248/314; 248/205.1; 128/205.13
(58) Field of Classification Search ............... 248/314, 248/205.2, 205.1, 309.1, 309.2; 128/208.13
See application file for complete search history.

(56) References Cited

U.S. PATENT DOCUMENTS

| | | | | |
|---|---|---|---|---|
| 1,513,401 A | * | 10/1924 | Krick | 248/252 |
| 2,640,595 A | * | 6/1953 | Byford | 211/74 |
| D191,891 S | * | 12/1961 | Antonio | D19/79 |
| 3,321,068 A | * | 5/1967 | Beach | 206/306 |
| D214,105 S | * | 5/1969 | Cline | D19/36 |
| 3,482,809 A | * | 12/1969 | McCall, Jr. | 248/205.1 |
| 3,731,819 A | * | 5/1973 | Sandhage | 211/74 |
| 3,792,822 A | * | 2/1974 | Underhill | 242/594.5 |
| 4,025,015 A | * | 5/1977 | Kolic | 248/205.3 |
| D256,425 S | * | 8/1980 | Hayes | D8/71 |
| D285,344 S | * | 8/1986 | Olson | D24/127 |
| 4,986,504 A | * | 1/1991 | Gary | 248/205.3 |
| 5,232,103 A | * | 8/1993 | Koenig et al. | 211/69.5 |
| 5,762,063 A | * | 6/1998 | Coates et al. | 128/205.13 |
| 5,855,285 A | * | 1/1999 | Laird et al. | 211/70.6 |
| 6,135,403 A | * | 10/2000 | Goldstein | 248/253 |
| 6,352,229 B1 | * | 3/2002 | Adams | 248/316.7 |

* cited by examiner

*Primary Examiner*—Anita M. King
(74) *Attorney, Agent, or Firm*—Holland & Knight LLP

(57) ABSTRACT

A mount for temporarily securing the elements of a manual life-support system consisting of a ventilator bag and mask for use in health-care facilities which can conveniently and aseptically position such a life-support system, accommodating masks of several different sizes, so that the system is available for use for emergency purposes, can be maintained ideally with connection to a source of oxygen, yet in a manner which diminishes the likelihood of noscomial infection.

2 Claims, 2 Drawing Sheets

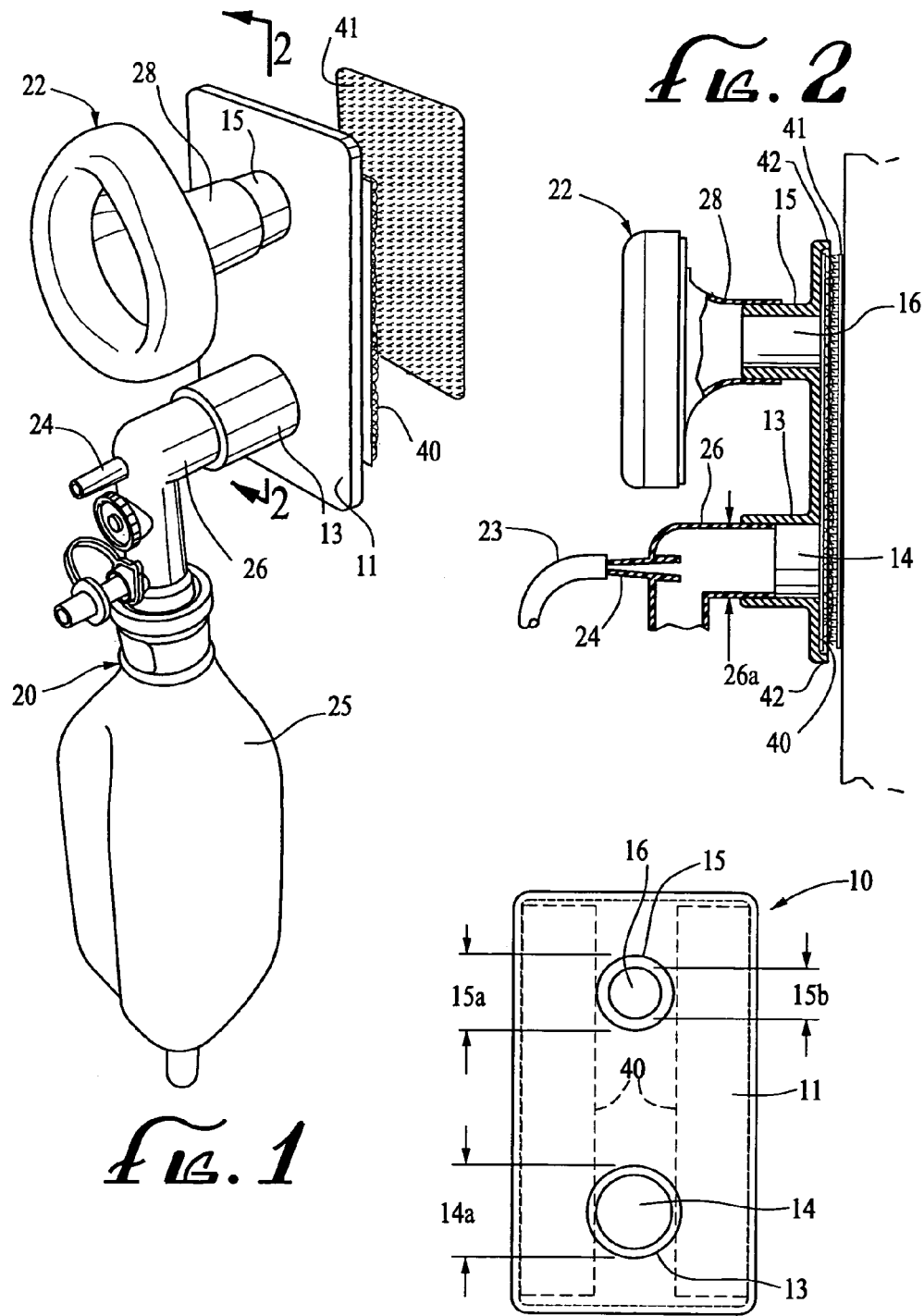

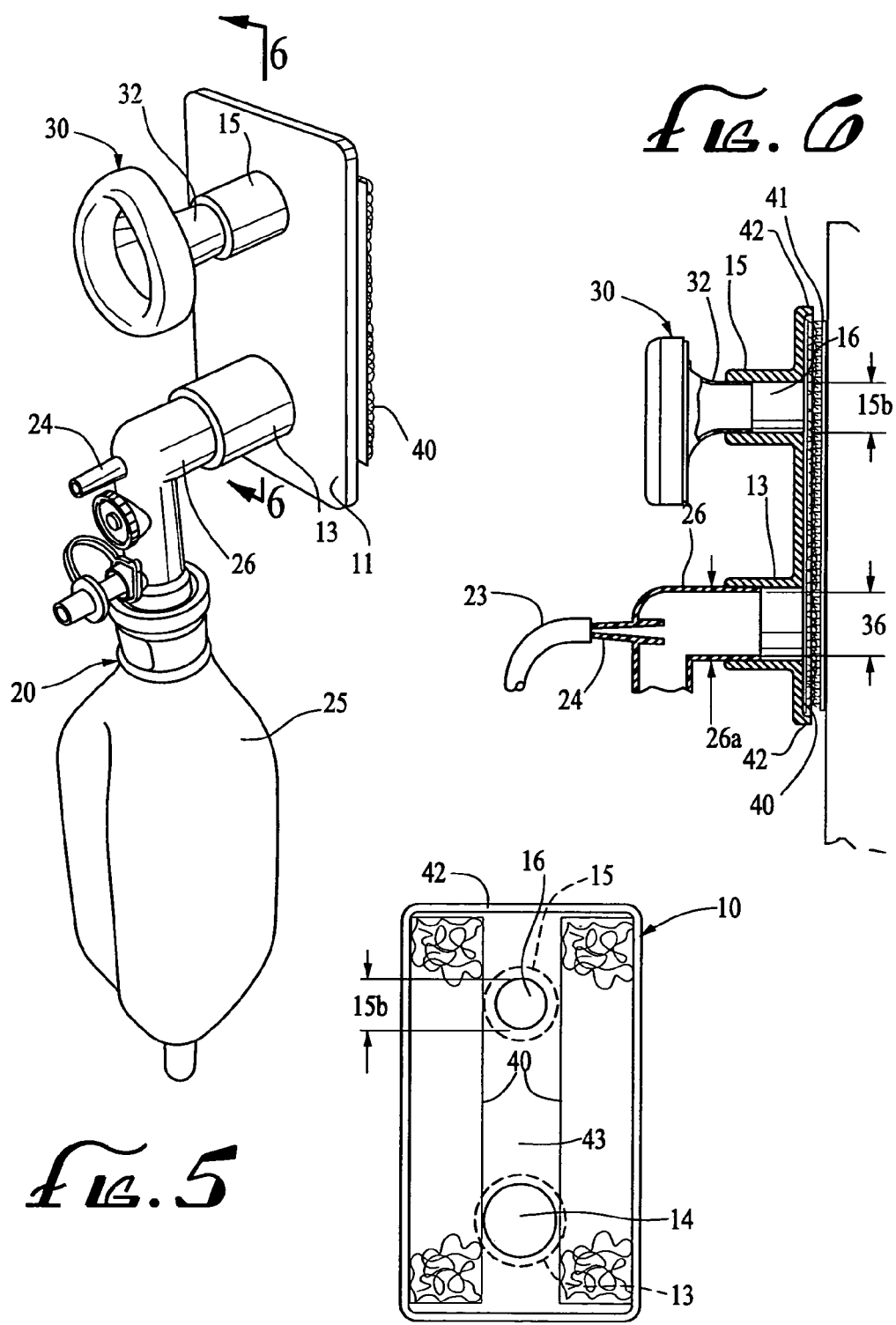

MEDICAL VENTILATOR BAG AND MASK MOUNT

BACKGROUND OF THE INVENTION

Field of the Invention

This invention relates generally to equipment used in health-care facilities and, in particular, to manual life-support systems. More particularly, this invention proposes a simple structure which has as its purpose to organize equipment in the area surrounding a patient's bed in a health-care facility and to hold the manual life-support systems consisting of a ventilator bag and face mask ready for use in a clean and convenient position.

Health-care facilities are required to have manual life-support systems closely available to any bed/patient that is being administered oxygen, whether the patient has been intubated or otherwise and, in particular, in intensive care and in pediatric/neonate facilities where newborns/children are maintained in isolettes or the like. In some health-care facilities, it is specifically required that a manual life-support system consisting of a face mask and positive pressure ventilator bag be connected to a source of oxygen and be spaced within four feet of the bed/patient. It is further a requirement that this life-support system be provided with a positive oxygen flow, i.e., that the oxygen flow be on at all times and that the flow be maintained at a specified rate. Gas suppliers and medical equipment suppliers do not provide a means to conveniently locate the ventilator bag/mask combination, and experience has been that the ventilator bag or mask is generally just placed upon the header, which carries various other oxygen or gas materials to the location of the bed. Essentially, the mask and ventilator bag are merely placed on a back shelf; where, of course, dust and dirt accumulate. In other instances, the mask and ventilator bag may be found resting on the foot of the patient's bed or somewhere else in the immediate vicinity of the patient. In still other instances, to obviate contamination, health care facilities may elect to keep the mask and bag combination in the sealed package in which they are provided by the medical supply company, which obviously diminishes its availability for emergencies.

In practice, some health-care workers prefer not to have oxygen freely flowing in the area due to safety concerns and for the further reason that an oxygen enriched atmosphere can enhance the growth of certain microorganisms. For these reasons plus what would appear to be the waste of the oxygen asset, many health-care workers will turn down or turn off the gas flow to the manual system. While this reduces risk of fire and other hazards, it effectively diminishes the value of this life-support system in emergency situations.

More importantly, the lack of a secure and clean method of positioning this equipment leads frequently to noscomial infections. Noscomial infections are those caused by a lack of cleanliness in the hospital environment. In this particular instance, the noscomial infection would be pulmonary in nature. If a patient sustains a pulmonary infection, it could typically add at least three days of bed-stay to a patient's confinement and possibly as many as 14 days. Not only does the health-care facility and others incur a possible legal risk when the facility's environment causes the infection, but the extended and unanticipated more lengthy bed-stay of the patient decreases hospital bed throughput as well as incurring additional medical treatment costs, which can be substantial.

The manual emergency life-support ventilator bags and masks are regularly recycled or disposed of in compliance with the infection control policy of the health care facility. Current practice is to dispose of the mask and ventilator bag either after a single patient use or after the expiration of seven days. It is contemplated that the mask and bag mounting system of the present invention can be manufactured at a sufficiently low cost and have ease of installation and use such that it too can be recycled on the same basis or the same period of time.

BRIEF SUMMARY OF THE INVENTION

The present invention solves the above-mentioned problems for health-care care facilities. This is accomplished by providing a simple mounting device, which can be located at or near the gas equipment at a location conveniently close to the bed/patient whereby the ventilator bag and face mask are mounted in a manner which is readily accessible. The mating apertures of the mask and ventilator bag are maintained in an aseptic condition and out of contact with dirt and dust or with other equipment in the patient area.

It is therefore an object of the present invention to provide a simple mask and ventilator bag mounting device, the principal purpose of which is to reduce noscomial pulmonary infections.

It is a further object of the present invention to provide a simple mask and ventilator bag mounting device which can be located conveniently near the bed/patient and the source of oxygen.

It is a further object of this invention to provide a mount that can accommodate different sizes of facial masks, which can be quickly assembled with the ventilator bag for emergency use.

It is another object of the present invention to provide a ventilator bag and mask mounting system wherein the oxygen can be maintained with a continuous gas flow as desired without creating a hazard or promoting excessive enhancement of certain microorganisms.

It is further an object of the present invention to provide a mask and ventilator bag mounting system so that the life-support system is conveniently located away from hostile environmental conditions and yet conveniently located to the bed/patient to maximize its efficient use in an emergency situation wherein gas flow is ideally maintained while awaiting use.

It is also an object of the present invention to provide a mask and ventilator bag mounting system which is low in cost and easily removed from its mounting place so as to be readily disposable on the same time schedule as the planned disposal scheme for the mask and ventilator bag themselves.

Accordingly, the invention comprises a flat backing plate or base having two cylindrical embossments preferably formed integrally therewith. The base may have any suitable means for affixing it to a wall or other surface, such as a simple bracket or by conventional hook and pile fasteners. Ventilator masks are currently provided with a single output tubing, the inside and outside diameters of which are standardized. There are three sizes of face masks: one for infants, one for pediatrics and one for adults. The adult and pediatric-size mask has an inlet tubing having a standardized inside diameter. The infant-size masks have a standardized outside diameter of a smaller size. The two cylindrical embossments are of different circumferential dimension. One embossment provides a cylindrical extension having an inside diameter to receive the outlet tube of the ventilator bag. The other embossment provides a cylindrical extension having an outside diameter which accommodates the inside diameter of the adult/pediatric mask, and an inside diameter to accommodate an infant mask. This embossment thus provides a mounting means to hold either an infant-size mask or a pediatric/adult-size mask. In this manner, a convenient mounting means is provided to hold the two parts of the emergency life-support system such that the interconnecting outlet and inlet extensions are maintained in an aseptic condition, the mask and bag are readily available and conveniently located near the bed/patient and will not come in contact with dust or dirt accumulated in the hospital environment; as the mask and ventilator bag are not laying on a shelf or bed or other possibly septic locations, yet are connected to a source of oxygen and can be readily assembled for use.

BRIEF DESCRIPTION OF THE DRAWINGS

FIG. 1 is a perspective view of the mounting system showing a ventilator bag and an adult-size mask mounted thereon and a preferred form of attaching the mount to another surface, such as a wall.

FIG. 2 is a partially sectioned view showing the interrelationship between the mounting embossments and portions of the ventilator bag and mask, the section taken along lines 2—2 of FIG. 1.

FIG. 3 is a front planar view of the mask mount showing a preferred form of the mounting means in dotted lines, being on the rear of the mount.

FIG. 4 is a rear view of the mount from that shown in FIG. 3 showing a preferred form of mounting means thereon.

FIG. 5 is a perspective view of the mount showing a ventilator bag attached thereto and an infant-size face mask mounted in the upper embossment.

FIG. 6 is a partially sectioned view taken along the 6—6 of FIG. 5 showing the interconnections between the ventilator bag and the infant-size face mask.

DETAILED DESCRIPTION OF THE INVENTION

Turning first to FIGS. 1 and 2, it should first be noted that the ventilator bag 20 and the face mask 22 are not a part of this invention but rather are standardized units manufactured in large quantities for the health-care industry. To understand the invention, however, it is necessary to describe these articles in some degree. The ventilator bag has an oxygen connection inlet 24, which is customarily affixed to a tubing 23 supplying a flow of oxygen. The lower portion of ventilator bag 20 includes an expandable bag 25, the purpose of which is to maintain an essentially constant pressure of oxygen when the bag is in use with a face mask attached and the mask placed over the nose and mouth of the patient. The upper portion of the ventilator bag assembly has an outlet tube 26.

Turning now to FIG. 3, the mask mount 10 consists of a flat or planar base 11 preferably formed integrally with two embossments 13 and 15. Embossments 13 and 15 are cylindrical in shape, and the central bore of each is open through the base 11 so that the central passages 14 and 16, respectively, extend all the way through the base.

The inside diameter 14a of embossment 13 is formed such that it has the same general dimension and configuration as the outside diameter 26a of outlet tube 26 such that, as shown in FIGS. 1 and 2, outlet tube 26 fits snugly within passage 14 of embossment 13. By being so placed, the exterior surface of outlet tube 26 is maintained free of dirt and dust and in a generally aseptic condition.

The adult face mask 22, normally of a soft pliable rubber-like material, has an inlet tube 28. The outside diameter 15a of embossment 15 is formed such that it has the same general dimension and configuration as the inside diameter of mask inlet tube 28. Thus, as seen in FIG. 2, mask inlet tube 28 extends snugly over the outside of embossment 15. In this mounted condition, the inside mating surface of the mask inlet tube 28 is kept free of dirt or dust and maintained in a generally aseptic condition.

Turning now to the second page of drawings, like numbers indicate similar or substantially identical structures as that shown in FIGS. 1 through 3. In FIGS. 5 and 6, however, it will be noted that face mask 30 is of smaller size, this being the infant/neonate face mask. The infant-size face mask has a mask inlet tube 32 of significantly smaller dimension than inlet tube 28 accommodate not only the smaller size of the infant face mask but also to differentiate it from face masks intended for adults.

As shown in FIG. 6, the ventilator bag outlet tube 26 has an outside diameter 26a that is of the same general dimension and configuration as the inside diameter 14a of embossment 13. As further shown in FIG. 6, ventilator bag outlet tube 26 also has an inside bore designated 36. The inside diameter 15b of embossment 15 is selected to have the same general dimension and configuration as the outside diameter of inlet tube 32 of mask 30, and not coincidentally, substantially the same as that of inside bore 36. In standardized fashion, the inside diameter of bore 36 is sized to receive the outside diameter of infant-size mask inlet tube 32 therein. Thus, on the mount 10, mask 30's inlet tube 32 fits snugly inside of inside diameter 15b of bore 16 of embossment 15. In this configuration, again the mating surfaces of inlet 32 and ventilator mask outlet 26 are both maintained in an environment free of dirt and dust and in a generally aseptic condition.

It may, at the same time be noted that in this case, the inside diameter 14a of embossment 13 will be substantially equal to the outside diameter 15a of embossment 15.

As will be well understood by those skilled in the art and from the relative dimensions disclosed herein, inlet tube 28 adult-size mask 22 fits over the outlet 26 of ventilator bag 20. When an emergency situation arises and the manual life-support system is needed, mask 22 is communicated with ventilator bag 20 by slipping extension tube extension tube 26.

Similarly, in the case of the infant mask, when it is desired to use the manual life-support system, the inlet tube 32 of mask 30 is inserted inside bore 36 of outlet tube 26 of ventilator bag 20. In this way, ventilator bags of standardized construction and size can be mounted for use with either adult, pediatric or infant life-support masks using a single mount, even though the actual face mask itself is of different sizes for infants, children or adults to accommodate their respective anatomies.

In addition to providing a mount to position a life-support system in a convenient location, oxygen can be supplied having a positive flow through tubing 24 without spreading oxygen around in areas of the patient locale as would cause increased hazardous conditions. More toward this purpose, a preferred mounting means and configuration of the back of the base 11 will be described.

Although there are several ways of affixing the mount to a convenient surface, such as a wall, which would permit ease of attachment and removal, FIGS. 1 and 4 both suggest a preferred means of affixing the mount. FIG. 1 shows a conventional hook-and-pile combination 40 and 41, whereby the pile portion 41 can be affixed to a wall and the hook arrangement 40, attached to the rear of base 11, can be pushed up against it and secured in place until replacement is desired. FIG. 4 shows a rear view of the mask mount, wherein the hook material of the hook-and-pile fastener is shown at 40.

The strips of hook material 40 form a passageway 43 there between communicating the openings 16 and 14. A depending flange 42 is preferably provided on the periphery of base 11, thereby surrounding the passageway 43. In this configuration oxygen coming through outlet 26 of ventilator bag 20 can flow easily through passage 14 to the back of base 11, up along passageway 43, such that a significant portion of the oxygen will flow out passage 16 and through the mask, which helps to keep it free of dust and other aerosols. The attachment means of this preferred embodiment is resilient, and is somewhat compressed when placed against the wall, which assures that most of the oxygen flows out through the mask and less escapes around the edges of the mount. This is may be assured by flange 42 extending around the entire periphery of base 11.

The economic advantages of the present invention are believed to be substantial. For, example the mounting device 10 can be inexpensively molded in one piece and provided with any suitable affixing means at relatively low cost. As previously related, it is the custom and practice in the health-care industry that a manual life-support system is disposed of either after a single patient use or after seven days' time, whichever occurs first. It is contemplated, therefore, that the entire mask, ventilator bag and the mount of this invention could be supplied as a combined unit and be disposed of on the same time schedule, providing only a very small cost increment to the health-care agency or patient. This increased cost is believed to be marginal compared to the expense of a single instance of noscomial pulmonary infection. As stated previously herein, a pulmonary infection can add a minimum of three days bed-stay to a patient's confinement. Assuming the economic penalty to a health-care facility of one such infection case to be estimated to average approximately $2,800 per day (which figure does not include any possible results of litigation over the matter), it would appear to be far more economical to add this small incremental expense for disposable mounts if they could materially reduce the onset of noscomial pulmonary infections. At the same time, having a mask mounted on a nearby wall or other surface, with a positive flow of oxygen maintained, as is desired, the life-support system is more readily available for use on short notice.

Although there is presently no immediate database that would support the assertion of reduced costs to health-care operations due to reduced pulmonary noscomial infections, there is a high probability of that reduction. It is entirely likely that institutions using the device will experience a reduction in the range of statistical probability of noscomial pulmonary infections and, after sufficient time has elapsed to build a database, a reduction in the mean average can be demonstrated.

Although the present invention has been described by way of exemplary embodiments, it should be understood that many changes and substitutions may be made by those skilled in the art without departing from the spirit and the scope of the present invention, which is defined by the appended claims.

What is claimed is:

1. An emergency life-support system, the combination comprising:
   a ventilator bag having an air outlet tube of a fixed outer diameter and a facemask having an air inlet tube defining an inner diameter and an outer diameter;
   a mount for said ventilator bag and said facemask comprising a base member, a first cylindrical embossment and a second cylindrical embossment;
   said first cylindrical embossment defining an inner diameter and an outer diameter and being carried by and projecting outwardly from said base member, said outer diameter of said first embossment being substantially equal to an inner diameter of said inlet tube of an adult size facemask, said inner diameter of said first embossment being substantially equal to an outer diameter of an inlet tube of an infant size facemask; and
   said second cylindrical embossment carried by and projecting outwardly from said base member in spaced disposition thereon from said first embossment and wherein said second embossment defines an inner diameter substantially equal to said outer diameter of said first embossment.

2. An emergency life-support system, the combination comprising:
   a ventilator bag having an air outlet tube of a fixed outer diameter and a facemask having an air inlet tube defining an inner diameter and an outer diameter;
   a mount for said ventilator bag and said facemask comprising a base member, a first cylindrical embossment and a second cylindrical embossment;
   said first cylindrical embossment defining an inner diameter and an outer diameter and being carried by and projecting outwardly from said base member, said outer diameter of said first embossment being substantially equal to an inner diameter of said inlet tube of an adult size facemask, said inner diameter of said first embossment being substantially equal to said outer diameter of an inlet tube of said infant size facemask; and
   said second cylindrical embossment carried by and projecting outwardly from said base member in spaced disposition thereon from said first embossment and wherein said second embossment defines an inner diameter substantially equal to a fixed outer diameter of an air outlet tube of a ventilator bag whereby a ventilator bag can be releasably secured to said second embossment.

* * * * *